(12) United States Patent
Rother et al.

(10) Patent No.: US 6,375,861 B1
(45) Date of Patent: *Apr. 23, 2002

(54) COMBINATION OF ACTIVE SUBSTANCES

(75) Inventors: Heinz-Joachim Rother, Krefeld; Martin Kugler, Leichlingen; Hartmut Rehbein, Krefeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/569,067

(22) Filed: May 11, 2000

Related U.S. Application Data

(62) Division of application No. 09/213,584, filed on Dec. 17, 1998, now Pat. No. 6,083,414, which is a division of application No. 08/952,413, filed as application No. PCT/EP96/01845 on May 3, 1996, now Pat. No. 5,888,415.

(30) Foreign Application Priority Data

May 16, 1995 (DE) ......... 195 17 840

(51) Int. Cl.⁷ .................. C14C 9/00
(52) U.S. Cl. .......... 252/8.57; 8/94.1 R; 8/94.18; 106/15.05; 106/18.32; 106/18.35; 424/405
(58) Field of Search ........... 252/8.57; 8/94.1 R, 8/94.18; 106/15.05, 18.32; 424/405

(56) References Cited

U.S. PATENT DOCUMENTS

| | | |
|---|---|---|
| 2,904,392 A | 9/1959 | Pomerantz et al. ........... 422/23 |
| 5,223,524 A | 6/1993 | Valcke ........... 514/383 |
| 5,374,378 A | 12/1994 | Lorentzen et al. .......... 252/380 |
| 5,378,406 A | 1/1995 | Nagaoka .............. 524/94 |
| 5,888,415 A * | 3/1999 | Rother et al. .......... 252/8.57 |
| 6,080,776 A * | 6/2000 | Assman et al. .......... 514/394 |
| 6,083,414 A * | 7/2000 | Rother et al. .......... 252/8.57 |

FOREIGN PATENT DOCUMENTS

| | | |
|---|---|---|
| EP | 341 954 | 11/1989 |
| EP | 366 071 | 5/1990 |
| EP | 409 500 | 1/1991 |

OTHER PUBLICATIONS

Derwent Abstract No. 95–118959 which is an abstract of Japanese Patent Spec. No. 07–041800. (Feb. 1995).

WPIDS Abstract No. 80–588956C which is an abstract of German Patent Spec. No. 2904390. (Aug. 1980).

WPIDS Abstract No. 96–131177, abstract of Spanish Patent Application No. 2081262. (Feb. 1996).

* cited by examiner

*Primary Examiner*—Anthony Green
(74) *Attorney, Agent, or Firm*—Norris, McLaughlin & Marcus

(57) ABSTRACT

The present application relates to the use of combinations of active compounds composed of phenolic active compounds and azole compounds for the preservation of animal hides and leather.

6 Claims, No Drawings

COMBINATION OF ACTIVE SUBSTANCES

This application is a divisional of application Ser. No. 09/213,584, filed Dec. 17, 1998, U.S. Pat. No. 6,083,414, issued on Jul. 4, 2000, which is a divisional of application Ser. No. 08/952,413, filed Nov. 13, 1997, U.S. Pat. No. 5,888,415, issued on Mar. 30, 1999 which is a 371 of PCT/EP96/01845 filed May 3, 1996.

The present application relates to the use of active compound combinations of phenolic active compounds with azole compounds for the preservation of animal hides and leather.

It is known that phenol derivatives and mixtures or formulations thereof can be used as products for the protection of materials in leather production. However, it has emerged that these compounds, used alone or in combination, do not provide sufficient protection against infections with microbes when storing hides and leather for a prolonged time.

Surprisingly, it has now been found that benzimidazoles, imidazoles, triazoles and/or morpholine derivatives in combination with phenolic compounds allow outstanding, long-term protection of the animal skins and leather during production and storage.

The invention therefore relates to the use of a combination of at least one triazole and/or at least one benzimidazole and/or at least one imidazole and/or at least one morpholine derivative with at least one phenolic compound for the protection of animal hides and leather during production and storage.

Suitable phenolic active compounds are preferably phenol derivatives, such as tribromophenol, trichlorophenol, tetrachlorophenol, nitrophenol, 3-methyl-4-chloro-phenol, 3,5-dimethyl-4-chlorophenol, phenoxyethanol, dichlorophene, o-phenyl-phenol, m-phenylphenol, p-phenylphenol, 2-benzyl-4-chlorophenol, 2,4-dichloro-3,5-dimethylphenol, 4-chlorothymol, chlorphen, triclosan, fentichlor and their ammonium, alkali metal and alkaline earth metal salts, and also their mixtures.

Suitable triazole compounds are preferably triazoles such as amitrole, azocyclotin, azaconazole, BAS 480F, bitertanol, cyproconazole, climbazole, difenoconazole, fenbuconazole, fen-chlorazole, fenethanil, fluquinconazole, flusilazole, flutriafol, hexaconazole, imiben-conazole, isazofos, myclobutanil, metconazole, epoxy-conazole, paclobutrazole, penconazole, propiconazole, cis-1-(4-chlorophenyl)-2-(1 H-1,2,4-triazol-1-yl)-cyclo-heptanol, tebuconazole, 2-(1-tert-butyl)-1-(2-chloro-phenyl)-3-(1,2,4-triazol-1-yl)-propan-2-ol, tetraconazole, triadimefon, triadimenol, triapenthenol, triflumizole, triticonazole, uniconazole and their metal salts and acid adducts, and also their mixtures.

Suitable imidazoles are preferably compounds such as imazalil, pefurazoate, prochloraz, triflumizole, bifonazole, canesten, fluotimazole, miconazole, econazole, isoconazole, sulconazole and their metal salts and adducts and also their mixtures.

Suitable benzimidazoles are preferably compounds such as methyl benzimidazolyl-carbamate (MC), benomyl, fuberidazole and thiabendazole.

Suitable morpholine derivatives are preferably compounds such as tridemorph, aldimorph, fenpropimorph, amorolfine and dodemorph.

Combinations of 3,5-dimethyl-4-chlorophenol, 2-benzyl-4-chlorophenol, p-chloro-m-cresol (CMC) and/or o-phenylphenol (OPP) as phenolic components and azoles such as tebuconazole, propiconazole, azaconazole, cyproconazole, climbazole, hexaconazole, epoxyconazole and/or imazalil as further components are preferred.

Combinations of the abovementioned preferred phenols with benzimidazoles such as MBC, benomyl and/or aldimorph or tridemorph are furthermore preferred.

Combinations of CMC and/or OPP with tebuconazole and/or propiconazole are particularly preferred.

Also preferred combinations are combinations of OPP and/or CMC with MBC.

In particular, a mixture comprising CMC, OPP and tebuconazole is used.

The mixing ratios of the phenolic component to the other active compounds is generally 5 to 200, preferably 10 to 100, in particular 12 to 50, parts by weight to 1 part by weight.

The ratio of the phenolic compounds to each other can be varied within wide limits and is preferably 1:1 to 1:5 in the case of a mixture of OPP and CMC.

The abovementioned mixtures of the active compounds are generally employed in the form of formulations. The use concentration is preferably 0.1 to 1% of mixture of active compounds based on the hides or leather to be protected.

In the compositions resulting from the formulation, the mixture of active compounds preferably amounts to 10 to 50%. The compositions comprise 10 to 30% of alkali metal hydroxides and/or alkaline earth metal hydroxides, 1 to 20% of ionic and/or non-ionic emulsifiers, 5 to 30% of organic solvents such as, in particular, glycols, ketones, glycol ethers, alcohols such as ethanol, methanol, 1,2-propanediol, n-propanol or 2-propanol, and 0–0.5% of perfumes and odoriferous substances as further components. The remainder to 100% is water.

The mixtures of active compounds and the compositions which can be prepared therefrom are used according to the invention in the production of leather for protecting animal hides against infection with, and damage caused by, microorganisms. The fact that representatives of the species Aspergillus niger, Aspergillus repens, Hormoconis resinae, Penicillium glaucum and Trichoderma viride, Penicillium species such as P. citrinum or P. glaucum, Paecilomyces variotii, Cladosporium species, and Mucor species, such as Mucor mucedo, Rhizopus species, such as Rhizopus oryzae and Rhizopus rouxii can be suppressed completely and long-term is of particular interest.

The examples which follow are intended to illustrate the invention and are not limited thereto.

EXAMPLE 1

Agar plates are inoculated with conidia of the species Aspergillus niger, Aspergillus repens, Penicillium glaucum, Trichoderma viride and Hormoconis resinae. Pieces of wet chrome leather (wet blue) which have been treated with mixture I and mixture II are subsequently placed on the agar, and the samples are incubated for 28 days at 20 to 30° C. and a relative atmospheric humidity of 95%.

| Mixture I | Mixture II |
|---|---|
| 30 parts by weight of p-chloro-m-cresol | 23 parts by weight of p-chloro-m-cresol |
| 13 parts by weight of o-phenylphenol | 10 parts by weight of o-phenylphenol |
| | 2 parts by weight of tebuconazole |

In the case of the wet blues preserved with mixture I, mould had grown on the test bodies after an incubation time of only 10 days. In the case of mixture II, no infection is observed after an incubation time of 28 days.

What is claimed is:

1. A method of protecting animal hides and leather against microbial infection during production of leather or storage, said method comprising applying thereto a protective effective amount of a microbicidal composition comprising a mixture of A) at least one heterocyclic compound selected from the group consisting of triazoles, benzimidazoles, imidazoles and morpholines with B) at least one phenolic compound.

2. Method as claimed in claim 1, wherein the microbicidal composition comprises one or more phenolic compounds selected from the group consisting of tribromophenol, tetrachlorophenol, nitrophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4 chlorophenol, alkali metal salts of said phenolic compounds and alkaline earth metal salts of said phenolic compounds; one or more triazole compounds selected from the group consisting of amitrole, azocyclotin, azaconazole, bitertanol, cyproconazole, climbazole, difenoconazole, fenbuconazole, fenchlorazole, fenethanol, fluquinconazole, flusilazole, flutriafol, hexaconzole, imibenconazole, isazofos, myclobutanil, metconazole, epoxyconazole, paclobutrazole, penconazole, propiconazole, cis-1-(4-chlorophenyl)-2-(1H-1,2,4-triazol-1-yl)-cycloheptanol, tebuconazole, 2-(1-tert-butyl)-1-(2-chlorophenyl)-3-1,2,4-triazol-1-yl)-propan-2-ol, tetraconazole, triadimefon, triadimenol, triapenthenol, triflumizole, triticonazole, uniconazole, metal salts of said triazole compounds and acid adducts of said triazole compounds; one or more imidazole compounds selected from the group consisting of imazalil, pefurazoate, prochloraz, triflumizole, bifonazole, canesten, fluotimazole, miconazole, econazole, isoconazole, sulconazole, metal salts of said imidazole compounds and acid adducts of said imidazole compounds; one or more benzimidazole compounds selected from the group consisting of benomyl, fuberidazole, thiabendazole, metal salts of said benzimidazole compounds and acid adducts of said benzimidazole compounds; and/or one or more morpholine compounds selected from the group consisting of tridemorph, aldimorph, fenpropimorph, amorolfine and dodemorph.

3. Method according to claim 1, wherein the microbicidal composition comprises 5 to 200 parts by weight of said at least one phenolic compound to 1 part by weight of said at least one heterocyclic compound.

4. A microbicidal composition useful to provide long-term protection of animal hides and leather against microbes, said microbicidal composition comprising a synergistic amount therefor of a mixture of A) at least one heterocyclic compound selected from the group consisting of triazoles, benzimidazoles, imidazoles and morpholines with B) at least one phenolic compound.

5. Microbicidal composition as claimed in claim 4, which comprises one or more phenolic compounds selected from the group consisting of tribromophenol, tetrachlorophenol, nitrophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4-chlorophenol, alkali metal salts of said phenolic compounds and alkaline earth metal salts of said phenolic compounds; one or more triazole compounds selected from the group consisting of amitrole, azocyclotin, azaconazole, bitertanol, cyproconazole, climbazole, difenoconazole, fenbuconazole, fenchlorazole, fenethanol, fluquinconazole, flusilazole, flutriafol, hexaconzole, imibenconazole, isazofos, myclobutanil, metconazole, epoxyconazole, paclobutrazole, penconazole, propiconazole, cis-1-(4-chlorophenyl)-2-(1H-1,2,4-triazol-1-yl)-cycloheptanol, tebuconazole, 2-(1-tert-butyl)-1-(2-chlorophenyl)-3-(1,2,4-triazol-1-yl)-propan-2-ol, tetraconazole, triadimefon, triadimenol, triapenthenol, triflumizole, triticonazole, uniconazole, metal salts of said triazole compounds and acid adducts of said triazole compounds; one or more imidazole compounds selected from the group consisting of imazalil, pefurazoate, prochloraz, triflumizole, bifonazole, canesten, fluotimazole, miconazole, econazole, isoconazole, sulconazole, metal salts of said imidazole compounds and acid adducts of said imidazole compounds; one or more benzimidazole compounds selected from the group consisting of benomyl, fuberidazole, thiabendazole, metal salts of said benzimidazole compounds and acid adducts of said benzimidazole compounds; and/or one or more morpholine compounds selected from the group consisting of tridemorph, aldimorph, fenpropimorph, amorolfine and dodemorph.

6. Microbicidal composition according to claim 4, which comprises 5 to 200 parts by weight of said at least one phenolic compound to 1 part by weight of said at least one heterocyclic compound.

* * * * *